(12) United States Patent
Strupp et al.

(10) Patent No.: US 11,471,434 B2
(45) Date of Patent: Oct. 18, 2022

(54) TREATMENT FOR MIGRAINE

(71) Applicant: INTRABIO LTD., Begbroke (GB)

(72) Inventors: Michael Strupp, Munich (DE); Mallory Factor, Catherine, AL (US)

(73) Assignee: INTRABIO LTD., Oxfordshire (GB)

( * ) Notice: Subject to any disclaimer, the term of this patent is extended or adjusted under 35 U.S.C. 154(b) by 109 days.

(21) Appl. No.: 16/622,785

(22) PCT Filed: Jun. 25, 2018

(86) PCT No.: PCT/IB2018/054676
§ 371 (c)(1),
(2) Date: Dec. 13, 2019

(87) PCT Pub. No.: WO2018/229738
PCT Pub. Date: Dec. 20, 2018

(65) Prior Publication Data
US 2020/0253905 A1    Aug. 13, 2020

(30) Foreign Application Priority Data
Jun. 14, 2017  (GB) ..................... 1709459

(51) Int. Cl.
A61K 31/198    (2006.01)
(52) U.S. Cl.
CPC ................... A61K 31/198 (2013.01)
(58) Field of Classification Search
CPC .................................................. A61K 31/198
See application file for complete search history.

(56) References Cited

U.S. PATENT DOCUMENTS

| | | | |
|---|---|---|---|
| 9,283,181 B2 | 3/2016 | Calias et al. | |
| 2004/0127501 A1* | 7/2004 | Chen | A61P 27/02 514/252.19 |
| 2006/0128717 A1* | 6/2006 | Sun | A61P 25/24 546/256 |
| 2006/0235022 A1* | 10/2006 | Sun | A61P 1/08 514/252.03 |
| 2006/0235055 A1* | 10/2006 | Kyle | C07D 401/04 514/343 |
| 2006/0241117 A1* | 10/2006 | Sun | A61P 31/18 546/256 |
| 2007/0027159 A1* | 2/2007 | Kyle | A61P 25/02 514/332 |
| 2007/0032500 A1* | 2/2007 | Sun | A61P 1/00 514/255.03 |
| 2013/0123239 A1* | 5/2013 | Kurose | A61P 1/00 514/318 |
| 2013/0142888 A1 | 6/2013 | Rekik | |
| 2014/0350056 A1* | 11/2014 | Yu | C07D 417/12 435/375 |

FOREIGN PATENT DOCUMENTS

| | | | |
|---|---|---|---|
| EP | 0288447 A1 * | 10/1988 | .......... A61K 31/205 |
| EP | 0288447 A1 | 10/1988 | |
| WO | WO 2006036634 A2 | 4/2006 | |
| WO | WO 2008032222 A2 | 3/2008 | |
| WO | WO 2012064892 A1 * | 5/2012 | ......... A61K 31/4045 |
| WO | WO 2017182802 A1 | 10/2017 | |
| WO | WO 2018029657 A1 | 2/2018 | |
| WO | WO 2018029658 A1 | 2/2018 | |
| WO | WO 2019079536 A1 | 4/2018 | |
| WO | WO 2018178670 A1 | 10/2018 | |
| WO | WO 2019078915 A1 | 4/2019 | |
| WO | WO 2019159110 A1 | 8/2019 | |
| WO | WO 2020115715 A1 | 6/2020 | |
| WO | WO 2020178721 A1 | 9/2020 | |
| WO | WO 2020261230 A1 | 12/2020 | |
| WO | WO 2021144720 A1 | 7/2021 | |

OTHER PUBLICATIONS

Fernandez, Pharmacological agents for the prevention of vestibular migraine, The Cochrane database of systematic reviews, (Jun. 21, 2015), No. 6, pp. CD010600.*
Armstrong, C., "AAN/AHS Update Recommendations for Migraine Prevention in Adults," American Family Physician, 87(8):584-585, American Academy of General Practice, United States (2013).
Bartleson, J.D. and Cutrer F. M., "Migraine Update Diagnosis and Treatment," Minnesota Medicine, 93(5):36-41, Minnesota Medical Assn, United States (2010).
Berge, S.M., et al., "Pharmaceutical Salts," Journal of Pharmaceutical Sciences 66(1): 1-19, Wiley, United States (1977).
Bose, P. and Goadsby, P.J., "The Migraine Postdrome," Curr Opin in Neurol, 29(3):299-301, Wolters Kluwer Health, Inc., England (2016).
Bremova, T., et al., "Acetyl-dl-leucine in Niemann-pick Type C: A Case Series," Neurology, 85(16): 1368-1375, American Academy of Neurology, United States (2015).
Buzzi, M.G., et al., "Prodromes and The Early Phase of The Migraine Attack: Therapeutic Relevance," Functional Neurology, 20(4):179-183, CIC Edizioni Internazionali, Italy (2005).
Cheng, K.K., et al., "Highly Stabilized Curcumin Nanoparticles Tested in an in Vitro Blood-brain Barrier Model and in Alzheimer's Disease Tg2576 Mice," American Association of Pharmaceutical Scientists Journal (AAPSJ), 15(2):324-336, American Association of Pharmaceutical Scientists, United States (2013).

(Continued)

*Primary Examiner* — Svetlana M Ivanova
(74) *Attorney, Agent, or Firm* — Sterne, Kessler, Goldstein & Fox P.L.L.C.

(57) ABSTRACT

A first aspect of the invention relates to leucine, acetyl-leucine, or a pharmaceutically acceptable salt thereof, for use in treating or preventing a migraine, or one or more symptoms associated therewith. A second aspect of the invention relates to a method of treating or preventing a migraine, or one or more symptoms associated therewith, in a subject, said method comprising administering to the subject a therapeutically or prophylactically effective amount of leucine, acetyl-leucine, or a pharmaceutically acceptable salt thereof.

20 Claims, 1 Drawing Sheet

(56) References Cited

OTHER PUBLICATIONS

Colman, I., et al., "Parenteral Dexamethasone for Acute Severe Migraine Headache: Meta-analysis of Randomised Controlled Trials for Preventing Recurrence," British Medical Journal, 336(7657): 1359-1361, British Medical Association, England (Jun. 2008).

Derry, S., et al., "Diclofenac with or without an Antiemetic for Acute Migraine Headaches in Adults," The Cochrane Database of Systematic Reviews 2013(4): CD008783, Wiley, England (Apr. 2013).

Domitrz, I., et al., "Changes in Serum Amino Acids in Migraine Patients without and with Aura and their Possible Usefulness in the Study of Migraine Pathogenesis," CNS and Neurological Disorders Drug Targets, 14(3):345-349, Bentham Science Publishers, United Arab Emirates (2015).

Ferber-Viart, C., et al., "Effects of Acetyl-dl-leucine in Vestibular Patients: A Clinical Study Following Neurotomy and Labyrinthectomy," Audiology and Neurotology, 14(1): 17-25, Karger, Switzerland (2009).

Gilmore, B. and Michael, M., "Treatment of Acute Migraine Headache," American family physician, 83(3):271-280, American Academy of General Practice, United States (2011).

Gunther, L., et al., "N-Acetyl-L-Leucine Accelerates Vestibular Compensation after Unilateral Labyrinthectomy by Action in the Cerebellum and Thalamus," Public Library of Science One (PLoS 1), 10(3):e0120891, Public Library of Science, United States (2015).

Zwergal A., et al., "Sequential [$^{18}$F]FDG uPET Whole-brain Imaging of Central Vestibular Compensation: A Model of Deafferentation-induced Brain Plasticity," Brain Structure and Function, 221(1): 159-170, Springer-Verlag, Germany (2016).

International Search Report and Written Opinion for International Application No. PCT/IB2018/054676, European Patent Office, Netherlands, dated Oct. 17, 2018, 9 pages.

Kabanov, A.V. and Batrakova, E.V., "New Technologies for Drug Delivery Across the Blood Brain Barrier," Current Pharmaceutical Design, 10(12): 1355-1363, Bentham Science Publishers, United Arab Emirates (2004).

Kelman, L., "The Postdrome of the Acute Migraine Attack," Cephalalgia : Cephalalgia, 26(2):214-220, Blackwell Publishing Ltd, England (2006).

Kirthi, V., et al., "Aspirin with or without an Antiemetic For Acute Migraine Headaches in Adults," The Cochrane database of systematic reviews, (4), CD008041, Wiley, England (2010).

Lahde, A., et al., "Production of L-Leucine Nanoparticles Under Various Conditions Using an Aerosol Flow Reactor Method," Journal of Nanomaterials, vol. 2008, Article ID 680897, 9 pages, Hindawi Publishing Corporation, (2008).

Lempert, T., et al., "Vestibular Migraine: Diagnostic Criteria," Journal of Vestibular Research : Equilibrium & Orientation, 22(4): 167-172, IOS Press, Netherlands (2012).

Ory, D.S., et al., "Intrathecal 2-hydroxypropyl-β-cyclodextrin Decreases Neurological Disease Progression in Niemann-Pick Disease, Type C1: a Non-randomised, Open-label, Phase 1-2 Trial," Lancet, 390:1758-1768, Elsevier, England (2017).

Patel, M.M. and Patel, B.M., "Crossing the Blood-Brain Barrier: Recent Advances in Drug Delivery to the Brain," CNS drugs, 31(2): 109-133, Springer International Publishing, Switzerland (2017).

Pelz, J.O., et al., "Failure to Confirm Benefit of Acetyl-dl-leucine in Degenerative Cerebellar Ataxia: A Case Series," Journal of Neurology, 262(5): 1373-1375, Springer-Verlag, Germany (2015).

Rabbie, R., et al., "Ibuprofen With or Without an Antiemetic for Acute Migraine Headaches in Adults," The Cochrane database of systematic reviews, (10), CD008039, Wiley, England (2010).

Rossi, P., et al., "Prodromes and Predictors of Migraine Attack," Functional Neurology, 20(4): 185-191, CIC Edizioni Internazionali, Italy (2005).

Schniepp, R., et al. "Acetyl-DL-leucine improves gait variability in patients with cerebellar ataxia—a case series." Cerebellum & Ataxias 3: 1-4, BioMed Central, England (2016).

Strupp, M., et al., "Effects of Acetyl-dl-leucine in Patients with Cerebellar Ataxia: A Case Series," Journal of Neurology, 260(10):2556-2561, Springer-Verlag, Germany (2013).

Tepper, S.J. and Tepper D.E., "Breaking the Cycle of Medication Overuse Headache," Cleveland Clinic Journal of Medicine, 77(4):236-242, Cleveland Clinic Educational Foundation, United States (2010).

Vibert, N. and Vidal, P.P., "In Vitro Effects of Acetyl-dl-leucine(Tanganil) on Central Vestibular Neurons and Vestibulo-ocular Networks of the Guinea-pig," European Journal of Neuroscience, 13:735-748, Federation of European Neuroscience Societies (2001).

Kurokawa, K., et al.. "Migraine and vertigo: introduction to migrainous vertigo," *Journal of Clinical and Experimental Medicine* 255(7):757-761, Springer, Switzerland (2015).

Murofushi, T., "Migraine Associated Vertigo," *Equilibrium Res.* 70(3): 172-175, Japan Society for Equilibrium Research, Japan (2011).

English language Translation of Pertinent Portion of Office Action for Japanese Patent Application No. 2020-519196, dated Apr. 26, 2022, 5 pages.

Lempert, T., et al., "Vestibular Migraine: Diagnostic Criteria," *Journal of Vestibular Research* 22:167-172, IOS Press, (2012).

Olesen, J., et al., "The International Classification of Headache Disorders, 3rd edition (beta version)," *Cephalalgia* 33(9):629-808, International Headache Society, (2013).

\* cited by examiner

TREATMENT FOR MIGRAINE

FIELD OF THE INVENTION

The invention relates to leucine, acetyl-leucine, or pharmaceutically acceptable salts thereof, and specifically to their use in the treatment and/or prevention of migraine and symptoms associated therewith.

BACKGROUND

Globally about 15% of the population is affected by migraines. Migraines are characterized by recurrent moderate to severe headaches. Typically, the headaches affect one half of the head, are pulsating in nature, and last from 2 to 72 hours. Symptoms of migraine include nausea, vomiting, and sensitivity to light, sound or smell. The pain is often accentuated by physical activity.

About 15-30% of people with migraines experience migraines with an "aura", a short period of visual disturbance which signals that the headache will soon occur. Occasionally, an aura can occur with little or no subsequent headache. This is known as an acephalgic migraine or silent migraine. Subjects who suffer migraines with aura also frequently suffer migraines without aura. The severity of the pain, duration of the headache, and frequency of attacks are variable.

Migraines are understood to be caused by a mixture of environmental and genetic factors. Whilst the underlying mechanisms have not been fully elucidated, they are believed to involve the nerves and blood vessels of the brain. There are four possible phases to a migraine, although not all the phases are always experienced:
- the prodrome, which occurs hours or days before the headache;
- the aura, which immediately precedes the headache;
- the pain (or headache) phase; and
- the postdrome, (effects experienced following the end of a migraine).

Prodromal or premonitory symptoms typically occur from two hours to two days before the start of pain or the aura. Prodromal symptoms include altered mood, irritability, depression or euphoria, fatigue, craving for certain food(s), stiff muscles (especially in the neck), constipation or diarrhea, and sensitivity to smells or noise. Prodromal symptoms can occur in migraines with or without aura (Rae-Grant 2004; Buzzi 2005; Rossi 2005; Samuels 2009).

The aura phase is a transient focal neurological phenomenon that occurs before or during the headache (Aminoff 2009). An aura appears gradually over a number of minutes and generally lasts less than an hour. Symptoms can be visual, sensory or motor in nature. Visual effects are the most common (Olesen 2006).

Visual disturbances typically include an area of partial alteration in the field of vision which flickers (also known as a scintillating scotoma). These typically start near the centre of vision and then spread out to the sides with zigzagging lines. Some sufferers experience blurring, whilst others experience a decreased vision or blindness in half the visual field, usually on one side of the vertical midline (hemianopsia).

A sensory aura may include a feeling of pins-and-needles that begins on one side in the hand and arm and spreads to the nose-mouth area on the same side. Numbness usually occurs after the tingling has passed. Other symptoms of the aura phase include speech or language disturbances, dizziness and motor problems. Auditory hallucinations or delusions may also be experienced (Slap 2008).

In the pain phase, the headache is typically unilateral, throbbing, and moderate to severe in intensity (Tintinalli 2010). In other cases, the pain may be bilateral, particularly in those who have migraines without an aura. Less commonly, pain may occur primarily in the neck, or the back or top of the head.

The pain is frequently accompanied by nausea, vomiting, sensitivity to light, sensitivity to sound, sensitivity to smells, fatigue and/or irritability (Aminoff 2009). In a basilar migraine, a migraine with neurological symptoms related to the brain stem or with neurological symptoms on both sides of the body, common effects include a sense of the world spinning, light-headedness, and confusion. Nausea occurs in almost 90% of people, and vomiting occurs in about one-third. Other symptoms include blurred vision, nasal stuffiness, diarrhea, frequent urination, pallor, sweating, swelling or tenderness of the scalp and neck stiffness.

The migraine postdrome refers to symptoms occurring once the acute headache has settled (Bose 2016). Many report a sore feeling in the area where the migraine was, and some report impaired thinking for a few days after the headache has passed. The subject may feel tired or "hung over" and have head pain, cognitive difficulties, gastrointestinal symptoms, mood changes, and weakness (Kelman 2006).

The diagnosis of migraine is based on signs and symptoms. The diagnosis of migraine without aura can be made according to the so-called "5, 4, 3, 2, 1 criteria" (International Headache Society 2004):
- Five or more attacks—for migraine with aura, two attacks are sufficient for diagnosis;
- Four hours to three days in duration;
- Two or more of the following:
  - Unilateral (affecting half the head);
  - Pulsating;
  - Moderate or severe pain intensity;
  - Worsened by or causing avoidance of routine physical activity;
- One or more of the following:
  - Nausea and/or vomiting;
  - Sensitivity to both light (photophobia) and sound (phonophobia).

If someone experiences two of the following: photophobia, nausea, or inability to work or study for a day, the diagnosis is more likely.

Migraines can be divided into seven subclasses, some of which include further subdivisions:
- Migraine without aura, or "common migraine", involves migraine headaches that are not accompanied by an aura;
- Migraine with aura, or "classic migraine", usually involves migraine headaches accompanied by an aura. Less commonly, an aura can occur without a headache, or with a non-migraine headache. Two other varieties are familial hemiplegic migraine and sporadic hemiplegic migraine, in which a person has migraines with aura and with accompanying motor weakness. Another variety is basilar-type migraine, where a headache and aura are accompanied by difficulty speaking, world spinning, ringing in ears, or a number of other brainstem-related symptoms, but not motor weakness;
- Childhood periodic syndromes that are commonly precursors of migraine include cyclical vomiting (occasional intense periods of vomiting), abdominal migraine (abdominal pain, usually accompanied by nausea), and benign paroxysmal vertigo of childhood (occasional attacks of vertigo);

Retinal migraine involves migraine headaches accompanied by visual disturbances or even temporary blindness in one eye;

Complications of migraine describe migraine headaches and/or auras that are unusually long or unusually frequent, or associated with a seizure or brain lesion;

Probable migraine describes conditions that have some characteristics of migraines, but where there is not enough evidence to diagnose it as a migraine with certainty (in the presence of concurrent medication overuse);

Chronic migraine is a complication of migraines, and is a headache that fulfills diagnostic criteria for migraine headache and occurs for a greater time interval.

Conventional treatments for migraine include simple pain killers such as ibuprofen or paracetamol (acetaminophen) for the headache, and other medication for the nausea and the avoidance of triggers.

Recommended initial treatment for those with mild to moderate symptoms are simple analgesics such as non-steroidal anti-inflammatory drugs (NSAIDs) or the combination of paracetamol, aspirin, and caffeine (Gilmore 2011). Several NSAIDs, including diclofenac, ibuprofen and ketorolac have evidence to support their use (Rabbie 2013; Derry 2013; Gilmore 2011). Aspirin can also relieve moderate to severe migraine pain, with a similar effectiveness to sumatriptan (Kirthi 2013).

Triptans or ergotamines may be prescribed to sufferers where simple pain medications are ineffective. Triptans (e.g. sumatriptan) can be effective for both pain and nausea and are the initially recommended treatments for those with moderate to severe pain, or those with milder symptoms who do not respond to simple analgesics (Bartleson 2010). Most side effects of triptans are mild, however, rare cases of myocardial ischemia have occurred, thus these drugs are not recommended for people with cardiovascular disease, who have had a stroke, or have migraines that are accompanied by neurological problems. Triptans should also be prescribed with caution for those with risk factors for vascular disease. Triptans are not addictive, but may cause medication-overuse headaches if used more than ten days per month (Tepper 2010). Ergotamine and dihydroergotamine are older medications that are still prescribed for migraines (Bartleson 2010). They appear to be equally as effective as the triptans and have adverse effects that are typically benign.

Medications useful to prevent migraine attacks include metoprolol, valproate, topiramate, intravenous metoclopramide and intranasal lidocaine (Armstrong 2013; Gilmore 2011). Metoclopramide is the recommended treatment for those who present to the emergency department. Haloperidol may also be useful in this group. A single dose of intravenous dexamethasone, when added to standard treatment of a migraine attack, is associated with a 26% decrease in headache recurrence in the following 72 hours (Colman 2008).

Medications are more effective if used early on during an attack. The frequent use of medications may result in medication overuse headache, in which the headaches become more severe and more frequent. This may occur with triptans, ergotamines, and analgesics, especially opioid analgesics. Due to these concerns simple analgesics are recommended to be used three days per week at most.

In the light of the drawbacks associated with existing treatments, and given the prevalence of the condition in the general population, there is a continued need to develop alternative treatments for migraines, in particular, for the prophylactic treatment of the aura which has not been achieved using drugs known in the art to date. The present disclosure addresses this need for alternative treatments for migraines and describes leucine and acetyl-leucine, as well as pharmaceutically acceptable salts thereof, for use in treating or preventing migraines.

SUMMARY OF THE INVENTION

Thus, a first aspect of the invention relates to leucine, acetyl-leucine, or a pharmaceutically acceptable salt thereof, for use in treating or preventing a migraine, or one or more symptoms associated therewith.

A second aspect of the invention relates to a method of treating or preventing a migraine, or one or more symptoms associated therewith, in a subject, the method comprising administering to the subject a therapeutically or prophylactically effective amount of leucine, acetyl-leucine, or a pharmaceutically acceptable salt thereof.

DETAILED DESCRIPTION

The invention encompasses agents, compositions and methods for treating and/or preventing migraine in a subject.

Acetyl-DL-leucine has been used in France to treat acute vertigo since 1957 and has an excellent safety profile. Despite numerous hypotheses, including stabilization of membrane potential, its pharmacological and electrophysiological modes of action remain unclear (Vibert 2001, Ferber-Viart 2009). A FDG-µPET study in a rat model of an acute unilateral labyrinthectomy (Zwergal, 2016) showed a significant effect of an L-enantiomer, N-acetyl-L-leucine, on postural compensation by activation of the vestibulo-cerebellum and a deactivation of the posterolateral thalamus (Gunther 2015). The improvement of cerebellar symptoms in a case series with cerebellar patients of different etiologies (Strupp 2013) supports the therapeutic efficacy of acetyl-DL-leucine. Another case series did not find benefit (Pelz 2015). Quantitative gait analysis showed that acetyl-DL-leucine also improves gait variability in patients with cerebellar ataxia (Schniepp 2015). In a third recent study, in 12 patients with Niemann-Pick Type C (NPC) this agent caused significant improvement in ataxia (Bremova 2015). Furthermore, a PET study in patients with ataxia of different etiologies given acetyl-DL-leucine demonstrated an increased metabolism in the midbrain and lower brainstem in responders (Becker-Bense, 2015), which could explain the benefits observed.

However, to date there has been no suggestion that acetyl-leucine would have therapeutic applications in the treatment of migraines, or symptoms thereof, for example, auras. The present application has surprisingly shown that acetyl-leucine can be used to treat or prevent migraines. And, as set forth in the present disclosure, it has also been found that leucine or a pharmaceutically acceptable salt of the same can be used in the treatment of migraines, or symptoms thereof.

References to "leucine" and "acetyl-leucine" throughout include pharmaceutically acceptable salts of the same, even if not expressly stated.

A "subject", as used herein, may be a vertebrate, mammal or domestic animal. Hence, compositions according to the invention may be used to treat any mammal, for example livestock (e.g. a horse, cow, sheep or pig), pets (e.g. a cat, dog, rabbit or guinea pig), a laboratory animal (e.g. a mouse or rat), or may be used in other veterinary applications. Preferably, the subject is a human.

The term "treating", as used herein, refers to reducing the frequency of, alleviating or eliminating migraines, or one or more symptoms related thereto.

The term "preventing", as used herein, refers to preventing migraines, or one or more symptoms associated therewith. For all of the embodiments described herein, preferably the leucine, acetyl leucine, or pharmaceutically acceptable salt thereof, is used prophylactically.

As used herein, the term "alleviating" means rendering migraines, or one or more symptoms associated therewith, less severe or less intense than in the absence of treatment.

As used herein, the term "reducing the frequency of" means reducing the occurrence of migraines, or one or more symptoms associated therewith, within a particular time frame relative to the occurrence in the absence of treatment.

In one preferred embodiment, the leucine, acetyl-leucine, or pharmaceutically acceptable salt thereof reduces the frequency of, alleviates or eliminates one or more migraine symptoms selected from headache, tiredness, aura, nausea, vomiting, sensitivity to light, sensitivity to sound, sensitivity to smell, sweating, poor concentration, feeling hot or cold, abdominal pain and diarrhoea.

As used herein, a symptom associated with migraine includes any clinical or laboratory manifestation associated with a migraine and is not limited to what the subject can feel or observe.

One aspect of the invention relates to leucine, acetyl-leucine, or a pharmaceutically acceptable salt thereof, for use in treating, or more preferably preventing, an aura. To date, there have been no reports of drugs that are capable of specifically preventing an aura. Preferably, the aura is a visual aura.

Another aspect of the invention relates to leucine, acetyl-leucine, or a pharmaceutically acceptable salt thereof, for use in treating or preventing a migraine associated with an aura (for example, a "classic migraine").

Another aspect of the invention relates to leucine, acetyl-leucine, or a pharmaceutically acceptable salt thereof, for use in treating or preventing a migraine that is not associated with an aura (for example, a "common migraine").

Another aspect of the invention relates to leucine, acetyl-leucine, or a pharmaceutically acceptable salt thereof, for use in treating or preventing an aura associated with a migraine headache.

Another aspect of the invention relates to leucine, acetyl-leucine, or a pharmaceutically acceptable salt thereof, for use in treating or preventing an aura that is not associated with a migraine headache.

Another aspect of the invention relates to leucine, acetyl-leucine, or a pharmaceutically acceptable salt thereof, for use in treating or preventing a hemiplegic migraine. For this embodiment, the migraine typically comprises a headache and an aura that are accompanied by motor weakness.

Another aspect of the invention relates to leucine, acetyl-leucine, or a pharmaceutically acceptable salt thereof, for use in treating or preventing a sporadic hemiplegic migraine.

Another aspect of the invention relates to leucine, acetyl-leucine, or a pharmaceutically acceptable salt thereof, for use in treating or preventing a vestibular migraine. Vestibular migraines can be defined according to diagnostic criteria set forth by the International Classification Committee of the Bàràny Society (Lempert 2012) and are typically characterised by:

A. At least 5 episodes with vestibular symptoms (as defined by the Bàràny Society's Classification of Vestibular Symptoms) of moderate or severe intensity, lasting 5 minutes to 72 hours;

B. Current or previous history of migraine with or without aura according to the International Classification Headache Disorders (ICHD);

C. One or more migraine features with at least 50% of the vestibular episodes:
   headache with at least two of the following characteristics: one sided location, pulsating quality, moderate or severe pain intensity, aggravation by routine physical activity;
   photophobia and phonophobia;
   visual aura;

D. Not better accounted for by another vestibular or ICHD diagnosis.

Another aspect of the invention relates to leucine, acetyl-leucine, or a pharmaceutically acceptable salt thereof, for use in treating or preventing a migraine that is not a vestibular migraine or that is not a vestibular migraine associated with symptoms of vertigo.

Another aspect of the invention relates to leucine, acetyl-leucine, or a pharmaceutically acceptable salt thereof, for use in treating or preventing a migraine that is not associated with vertigo or symptoms of vertigo. In some embodiments, the migraine is not associated with acute vertigo or vertigo due to an acute peripheral vestibular lesion. In some embodiments, the migraine is not associated with Meniere's vertigo or vertigo of inflammatory (vestibular neuritis) or toxic origin.

Another aspect of the invention relates to leucine, acetyl-leucine, or a pharmaceutically acceptable salt thereof, for use in treating or preventing a basilar-type migraine. For this embodiment, the migraine typically comprises a headache and an aura that are accompanied by one or more of the following symptoms: difficulty speaking, world spinning, ringing in ears, and other brainstem-related symptoms.

Another aspect of the invention relates to leucine, acetyl-leucine, or a pharmaceutically acceptable salt thereof, for use in treating or preventing a retinal migraine. For this embodiment, the retinal migraine typically includes headaches accompanied by visual disturbances or temporary blindness.

Another aspect of the invention relates to leucine, acetyl-leucine, or a pharmaceutically acceptable salt thereof, for use in treating or preventing chronic migraine. As used herein, the term "chronic migraine" refers to a subject suffering more than fifteen headache days per month over a three month period of which more than eight are migrainous, in the absence of medication (as defined by The International Headache Society).

Another aspect of the invention relates to leucine, acetyl-leucine, or a pharmaceutically acceptable salt thereof, for use in treating or preventing episodic migraine. As used herein, "episodic migraine" refers to a subject suffering less than fifteen headache days per month over a three month period, in the absence of medication (as defined by The International Headache Society).

Another aspect of the invention relates to leucine, acetyl-leucine, or a pharmaceutically acceptable salt thereof, for use in treating or preventing acute migraine.

Another aspect of the invention relates to leucine, acetyl-leucine, or a pharmaceutically acceptable salt thereof, for use in treating or preventing one or more prodromal symptoms associated with a migraine. Preferably, the prodromal symptoms are selected from one or more of altered mood, irritability, depression or euphoria, fatigue, craving for certain food(s), stiff muscles (especially in the neck), constipation, diarrhea, and sensitivity to smells and noise Another aspect of the invention relates to leucine, acetyl-leucine, or a pharmaceutically acceptable salt thereof, for use in treating or preventing pain associated with a migraine.

Another aspect of the invention relates to leucine, acetyl-leucine, or a pharmaceutically acceptable salt thereof, for use in treating or preventing one or more postdromal symptoms associated with a migraine. Preferably, the postdromal symptoms are selected from one or more of soreness in the area where the migraine was, impaired thinking, tiredness, head pain, cognitive difficulties, gastrointestinal symptoms, mood changes and weakness.

In one preferred embodiment, the leucine, acetyl-leucine, or a pharmaceutically acceptable salt thereof reduces, alleviates or eliminates migraine headaches.

In one preferred embodiment, the leucine, acetyl-leucine, or a pharmaceutically acceptable salt thereof reduces, alleviates or eliminates aura. More preferably, the leucine, acetyl-leucine, or a pharmaceutically acceptable salt thereof reduces the frequency of, alleviates or eliminates one or more symptoms selected from visual problems or visual disturbances, numbness or tingling, dizziness, balance problems, motor problems, speech difficulties and loss of consciousness. Preferably, the leucine, acetyl-leucine, or a pharmaceutically acceptable salt thereof, prevents an aura from occurring, for example, by preventing one or more of the above-mentioned symptoms from occurring.

In accordance with a second aspect of the invention, there is provided a method of treating or preventing a migraine, or one or more symptoms associated therewith, in a subject, the method comprising administering a therapeutically or prophylactically effective amount of leucine, acetyl-leucine, or a pharmaceutically acceptable salt thereof, to the subject.

Preferred features for the first aspect of the invention are also applicable to the second aspect.

Another aspect of the invention relates to a method of treating or preventing a migraine that is not a vestibular migraine, or that is not a vestibular migraine associated with symptoms of vertigo, in a subject, the method comprising administering a therapeutically or prophylactically effective amount of leucine, acetyl-leucine, or a pharmaceutically acceptable salt thereof, to the subject.

Another aspect of the invention relates to a method of treating or preventing a migraine that is not associated with vertigo, or symptoms of vertigo in a subject, the method comprising administering a therapeutically or prophylactically effective amount of leucine, acetyl-leucine, or a pharmaceutically acceptable salt thereof, to the subject.

A "therapeutically effective amount" or a "prophylactically effective amount" of an agent is any amount which, when administered to a subject, is the amount of agent that is needed to produce the desired effect. The dose may be determined according to various parameters, especially according to the specific form of leucine or acetyl-leucine used; the age, weight and condition of the patient to be treated; the route of administration; and the required regimen. A physician will be able to determine the required route of administration and dosage for any particular patient. A typical daily dose may be from about 10 to 225 mg per kg, from about 10 to 150 mg per kg, preferably from about 10 mg/kg to 100 mg/kg of body weight. For example, the prophylactically effective amount of acetyl-leucine used may be between 0.5 g and 15 g per day, or between 1 g and 10 g per day, preferably between 1.5 g and 7 g per day. Further details on dosages are provided below.

Leucine, Acetyl-Leucine, and Compositions Thereof

Acetyl-leucine in racemic form and salts of the same are known for their effectiveness in the symptomatic treatment of vertigo of various origins, notably vertigo due to an acute peripheral vestibular lesion. Acetyl-leucine is marketed by Pierre Fabre Medicament in racemate form as an anti-vertigo medicament under the name Tanganil®. Clinical results relating to acetyl-leucine reported by various authors demonstrate an improvement in vertigo symptomology in more than 95% of cases, including the disappearance of vertigo attacks.

In one preferred embodiment, the leucine, acetyl-leucine, or pharmaceutically acceptable salt thereof, is in racemic form, which means that the compound comprises about equal amounts of enantiomers. Alternatively the leucine or acetyl-leucine may be present in an enantiomeric excess of either the L-enantiomer or the D-enantiomer. The racemic and enantiomeric forms may be obtained in accordance with known procedures in the art.

In one particularly preferred embodiment, the leucine, acetyl-leucine, or pharmaceutically acceptable salt thereof, is in the form of the L-enantiomer.

In another embodiment, the leucine, acetyl-leucine, or pharmaceutically acceptable salt thereof, is in the form of the D-enantiomer.

Preferably, the leucine or acetyl-leucine is in free base form.

The leucine, acetyl-leucine, or a pharmaceutically acceptable salt thereof, may be formulated and administered to a subject in accordance with known teachings in the art.

The leucine, acetyl-leucine, or a pharmaceutically acceptable salt of the same, may thus be formulated as a pharmaceutical composition, optionally comprising one or more pharmaceutically acceptable carriers, diluents or excipients.

The active agent (composition) may be used in a monotherapy (i.e. use of the active agent alone) for treating migraine in a subject. Alternatively, the active agent (composition) may be used as an adjunct to, or in combination with, known therapies, for treating migraine in a subject.

The active agent (composition) may take any of a number of different forms depending, in particular, on the manner in which it is to be used. Thus, for example, the agent or composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the carrier of the pharmaceutical composition according to the invention should be one which is well-tolerated by the subject to whom it is given.

A "pharmaceutically acceptable carrier" as referred to herein, is any known compound or combination of known compounds that are known to those skilled in the art to be useful in formulating pharmaceutical compositions.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

Examples of such suitable excipients for the various different forms of pharmaceutical compositions described herein may be found in the "Handbook of Pharmaceutical Excipients, $2^{nd}$ Edition, (1994), Edited by A Wade and P J Weller. Examples of such excipients are gelatin, gum arabicum, lactose, microcrystalline cellulose, starch, sodium starch glycolate, calcium hydrogen phosphate, magnesium stearate, talcum, colloidal silicon dioxide and the like.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In one preferred embodiment, the pharmaceutically acceptable carrier may be a solid, and the composition may be in the form of a powder or tablet. A solid pharmaceutically acceptable carrier may include one or more substances which may also act as flavouring agents, buffers, lubricants, stabilizers, solubilizers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier is a finely divided solid that is in admixture with the finely divided active agents according to the invention. In tablets, the active agent may be mixed with a carrier having the necessary compression properties in suitable proportions and compacted in the shape and size desired. The powders and tablets preferably contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

In another preferred embodiment, the pharmaceutically acceptable carrier may be a liquid, and the pharmaceutical composition is in the form of a solution. Liquid carriers are used in preparing solutions, suspensions, emulsions, syrups, elixirs and pressurized compositions. The active agent according to the invention may be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurised compositions can be a halogenated hydrocarbon or other pharmaceutically acceptable propellant.

Liquid pharmaceutical compositions, which are sterile solutions or suspensions, can be utilised by, for example, intramuscular, intrathecal, epidural, intraperitoneal, intravenous and particularly subcutaneous injection. The active agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Leucine, acetyl-leucine, and compositions comprising the same may alternatively be administered by inhalation (e.g. intranasally). Compositions may also be formulated for topical use. For instance, creams or ointments may be applied to the skin.

Leucine, acetyl-leucine according to the invention may be incorporated within a slow- or delayed-release device. Such devices may, for example, be inserted on or under the skin, and the medicament may be released over weeks or even months. Such devices may be particularly advantageous when long-term treatment with leucine or acetyl-leucine used according to the invention is required and which would normally require frequent administration (e.g. at least daily administration).

In one particularly preferred embodiment, the pharmaceutical composition is in the form of a tablet. In tablets, the active agent may be mixed with a vehicle having the necessary compression properties in suitable proportions and compacted in the shape and size desired. The tablets preferably contain up to 99% by weight of the active agent.

Thus, in a preferred embodiment, the leucine, acetyl-leucine, or a pharmaceutically acceptable salt of the same, is provided in a solid dosage form suitable for oral administration, preferably in the form of a tablet.

Pharmaceutical formulations in solid oral dosage form, such as tablets, may be prepared by any method known in the art of pharmacy. Pharmaceutical formulations are usually prepared by mixing the active substance, or a pharmaceutically acceptable salt thereof, with conventional pharmaceutically acceptable carriers, diluents or excipients.

A tablet may be formulated according to conventional methods known in the art and may be coated or uncoated. Tanganil®, for example, includes wheat starch, pregelatinized maize (corn) starch, calcium carbonate and magnesium stearate as excipients. The same, or similar, excipients may be employed in the present invention. The precise composition of each 700 mg Tanganil® tablet is as follows: 500 mg acetyl-DL-leucine, 88 mg wheat starch, 88 mg pregelatinized maize (corn) starch, 13 mg calcium carbonate and 11 mg magnesium stearate. The same tablets may be employed in the present invention. A generic version of such tablets may alternatively be used.

As discussed above, the leucine, acetyl-leucine, or pharmaceutically acceptable salt thereof may be formulated and administered as a pharmaceutical composition taking any number of different forms. For example, the leucine, acetyl-leucine or pharmaceutically acceptable salt thereof may be formulated as a pharmaceutical composition to facilitate its delivery across the blood-brain barrier. As a further example, the leucine, acetyl-leucine or pharmaceutically acceptable salt thereof may be formulated as a pharmaceutical composition for bypassing the blood-brain barrier. Formulations that facilitate delivery across the blood-brain barrier or that are suitable for administration in a manner that bypasses the blood-brain barrier may be used to prepare and administer leucine (not acetylated) as described herein. As demonstrated in the present disclosure, leucine exposure to cells exhibiting a lysosomal disease phenotype improved, like exposure to acetyl-leucine, the cellular dysfunction (e.g., by reducing lysosomal storage volumes towards control values), thereby demonstrating leucine's and acetyl-leucine's similar activity (see FIG. 1).

In one embodiment, the pharmaceutical composition (e.g., comprising leucine or salt thereof) is formulated for nanodelivery, e.g., colloidal drug-carrier systems. Suitable examples include but are not limited to liposomes, nanoparticles (e.g., polymeric, lipid and inorganic nanoparticles), nanogels, dendrimers, micelles, nanoemulsions, polymersomes, exosomes, and quantum dots. (See, e.g., Patel 2017; Kabanov 2004; Cheng 2013; Lähde 2008).

In one embodiment, the pharmaceutical composition (e.g., comprising leucine or a salt thereof) is formulated for direct delivery to the central nervous system (CNS), such as by injection or infusion. Formulations for and methods of direct delivery to the CNS are known in the art. (See, e.g., U.S. Pat. No. 9,283,181). Examples of such administration include but are not limited to intranasal, intraventricular, intrathecal, intracranial, and delivery via nasal mucosal grafting.

In one embodiment, the pharmaceutical composition is formulated for (and administered by) intranasal delivery. (See, e.g., Hanson 2008). In one embodiment, the pharmaceutical composition is formulated for (and administered by) delivery via a nasal mucosal graft. In one embodiment, the pharmaceutical composition is formulated for (and administered by) intracerebroventricular injection or infusion. In another embodiment, the pharmaceutical composition is formulated for (and administered by) intrathecal intracisternal injection or infusion. In one embodiment, the pharmaceutical composition is formulated for (and administered by) intrathecal lumbar injection or infusion. For example, the active agent may be formulated for intrathecal administration and/or administered intrathecally in the same or a similar manner discussed by Ory (2017).

Various techniques may be used including, without limitation, injection through a burrhole or cisternal or lumbar puncture or the like as known in the art. Various devices, whether internal (e.g., implanted) or external, may be used for delivery as known in the art, such as pumps, catheters, reservoirs, etc.

In one embodiment, the administration interval is once every two weeks. In one embodiment, the administration interval is once every month. In one embodiment, the administration interval is once every two months. In one embodiment, the administration interval is twice per month. In one embodiment, the administration interval is once every week. In one embodiment, the administration interval is twice or several times per week. In one embodiment, the administration interval is daily. In one embodiment, the administration is continuous, such as continuous infusion.

Leucine, or a pharmaceutically acceptable salt thereof, may be administered in a dose or amount equivalent to those disclosed herein for acetyl-leucine, adjusted to account for either its direct delivery to the CNS or its delivery across the blood-brain barrier.

Similarly, acetyl-leucine, or a pharmaceutically acceptable salt thereof may be administered in a dose or amount as disclosed herein; the dose may be adjusted according to its route of administration (e.g., direct delivery to the CNS).

Dosage

The leucine, acetyl-leucine, or pharmaceutically acceptable salt of the same, may be administered at a dose of from about 500 mg to about 15 g per day, or from about 500 mg to about 10 g per day, preferably from about 1.5 g to about 10 g per day. Preferably, the leucine, acetyl-leucine, or a pharmaceutically acceptable salt of the same, is administered by solid oral or liquid oral route.

At the start of treatment, or in the event of failure, the dosage may be safely increased up to 3 g, 4 g, 5 g, 6 g, 7 g, 8 g, 9 g, 10 g, 11 g, 12 g, 13 g, 14 g, 15 g per day.

If one enantiomer is administered, the doses may be reduced accordingly. For instance if only leucine, acetyl-L-leucine or if only acetyl-D-leucine is administered, the dose may be between 250 mg and 15 g per day, between 250 mg and 10 g per day, between 250 mg and 5 g per day, or preferably between 0.75 g and 5 g per day.

In accordance with the present invention, leucine, acetyl-leucine, or a pharmaceutically acceptable salt of the same, may be administered at a dose that is higher than previously known and/or for a treatment duration that is longer than previously known.

For example, in one preferred embodiment the administered dose is from about 1 g to about 15 g or from about 1 g to about 10 g per day, more preferably from about 1.5 g to about 7 g per day. Preferably, the administered dose may be between 2, 3, 4, 5, 6, 7, 8, 9, 10, 11, 12, 13, or 14 g and 15 g per day. More preferably, the administered dose may be between 2, 3, 4, 5, 6, 7, 8 or 9 g and 10 g per day. In one preferred embodiment, the administered dose may be more than 1.5 g per day, but less than 15, 14, 13, 12, 11, 10, 9, 8, 7, 6 or 5 g per day. In one preferred embodiment, the dose is in the range of more than 2 g to no more than 6 g per day. In a preferred embodiment, these doses are administered in a solid oral dosage form, preferably tablets. In a preferred embodiment, these doses are for leucine or acetyl-leucine when in its racemic form. Doses for leucine or acetyl-leucine when an enantiomeric excess is present may be lower than those recited here, for example, around 50% lower. The above recited dose-ranges when halved are thus also explicitly encompassed by the invention.

The total daily dose may be spread across multiple administrations, i.e. administration may be required two or more times a day to achieve the required dose. As an example, the required number of tablets to provide the total daily dose of leucine or acetyl-leucine may be split across two administrations (for example, in the morning and evening) or three administrations (for example, in the morning, noon and evening). Each dose is preferably administered with food. Thus, as an example, a total daily dose of 3 g acetyl-DL-leucine may be administered as two Tanganil® (or equivalent) tablets with breakfast, two further tablets with lunch and two further tablets with dinner.

In one preferred embodiment, the leucine, acetyl-leucine, or pharmaceutically acceptable salt thereof, is administered once a day.

In another preferred embodiment, the leucine, acetyl-leucine, or pharmaceutically acceptable salt thereof, is administered twice a day.

In another preferred embodiment, the leucine, acetyl-leucine, or pharmaceutically acceptable salt thereof, is administered three times a day, preferably morning, lunchtime and evening.

In one preferred embodiment, the leucine, acetyl-leucine, or pharmaceutically acceptable salt thereof, is administered in a dose of from about 500 mg to about 15 g per day.

In another preferred embodiment, the leucine, acetyl-leucine, or pharmaceutically acceptable salt thereof, is administered in a dose of from about 1500 mg to about 6000 mg per day.

In another preferred embodiment, the leucine, acetyl-leucine, or pharmaceutically acceptable salt thereof, is administered in a total daily dose of from about 2500 mg to about 5500 mg per day.

In one preferred embodiment, the leucine, acetyl-leucine, or pharmaceutically acceptable salt thereof, is administered in unit dosage form, wherein the unit dosage comprises 500 mg of active agent.

In one preferred embodiment, the leucine, acetyl-leucine, or pharmaceutically acceptable salt thereof, is administered in a total dose of about 3000 mg per day. More preferably, the leucine, acetyl-leucine, or pharmaceutically acceptable salt thereof, is administered in a dose of 1000 mg three times a day, preferably two 500 mg tablets, three times a day.

In another preferred embodiment, the leucine, acetyl-leucine, or pharmaceutically acceptable salt thereof, is administered in a total dose of about 4500 mg per day. More preferably, the leucine, acetyl-leucine, or pharmaceutically acceptable salt thereof, is administered in a dose of 1500 mg three times a day, preferably three 500 mg tablets, three times a day.

In another preferred embodiment, the leucine, acetyl-leucine, or pharmaceutically acceptable salt thereof, is administered in a total dose of about 5000 mg per day. More preferably, the leucine, acetyl-leucine, or pharmaceutically acceptable salt thereof, is administered in one dose of four 500 mg tablets, and two doses of three 500 mg tablets.

In another preferred embodiment, the leucine, acetyl-leucine, or pharmaceutically acceptable salt thereof, is administered in a total dose of about 5500 mg per day. More preferably, the leucine, acetyl-leucine, or pharmaceutically acceptable salt thereof, is administered in two doses of four 500 mg tablets, and one dose of three 500 mg tablets The treatment duration may vary according to clinical progression. For example, it may be seven days or more, two weeks or more, three weeks or more, one month or more, six weeks or more, seven weeks or more or two months or more. In one preferred embodiment, the leucine, acetyl-leucine, or pharmaceutically acceptable salt thereof, is administered for a treatment duration of two weeks or more.

In another preferred embodiment, the leucine, acetyl-leucine, or pharmaceutically acceptable salt thereof, is administered for three months or more, four months or more, five months or more or six months or more. In one preferred embodiment, the treatment duration is 1 year or more, 2 years or more, 4 years or more, 5 years or more, or 10 years or more. In one preferred embodiment, the treatment duration may be the life-time of the patient.

Any and all combinations of dosage form, dose amount, dosing schedule and treatment duration are envisaged and encompassed by the invention. A preferred combination is a total daily dose of between 2 g and 6 g per day, taken across three administrations per day, for a treatment duration of two months or more. A further preferred combination is a total daily dose of more than 3 g to no more than 5 g per day, taken across three administrations per day, for a treatment duration of six months or more. Preferably the dosage form is a solid oral dosage form, more preferably, tablets.

Salts

The agents of the invention can be present as salts, in particular pharmaceutically acceptable salts or esters.

Pharmaceutically acceptable salts of the agents of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Enantiomers/Tautomers

The invention also includes where appropriate all enantiomers and tautomers of the agents of the invention. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agents and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agents of the invention and pharmaceutically acceptable salts thereof of this invention can generally be prepared by conventional procedures using appropriate isotopic variations of suitable reagents.

Solvates

The present invention also includes solvate forms of the agent of the invention. The terms used in the claims encompass these forms.

Polymorphs

The invention furthermore relates to the agents of the invention in its various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

All of the features described herein (including any accompanying claims, abstract and drawings), and/or all of the steps of any method so disclosed, may be combined with any of the above aspects in any combination, except combinations where at least some of such features and/or steps are mutually exclusive.

The invention will now be explained in further detail by way of the following non-limiting Examples, which demonstrate the utility of, among other things, acetyl-leucine in treating migraine in a subject.

EXAMPLES

Example 1

Case Study: Administration of Acetyl-Leucine for Migraines

Tanganil® was obtained from Pierre Fabre Medicament (France) in tablet form.

Patient Details:
Sex: Female
Age: 18
Height: 1.75 m
Weight: 65 kg
Treatment:

Six tablets per day: two in the morning, two at noon and two in the evening. The precise composition of each 500 mg Tanganil® tablet is as follows: 500 mg acetyl-DL-leucine, 88 mg wheat starch, 88 mg pregelatinized maize (corn) starch, 13 mg calcium carbonate and 11 mg magnesium stearate.

Before treatment with Tanganil®, the subject experienced the following symptoms for approximately 6-9 months before treatment with Tanganil®:

Headache attacks lasting a few minutes to half an hour; on approximately 4-6 days a week; 1-4 times a day;

Sudden attacks of vertigo. During these attacks fast head movements often led to strong vertigo for a few seconds. Approximately 1-3 days per week; 1-2 times per day;

Nausea without any trigger for a few minutes to an hour. Nausea subsides when the patient lies down or with heat treatment. Approximately 4-6 days per week, usually in the evening;

Pain in and around the eyes/eye sockets when looking up or too far to the left or the right, sometimes lasting for a whole day. Approximately once every two weeks.

Prior to this 6-9 month period before treatment with Tanganil®, the subject occasionally had vertigo and nausea, but hardly ever headaches. After treatment with Tanganil®, the subject noticed a change after about two and a half weeks; most of the symptoms occurred only half as often. After four weeks of treatment, the subject noted:

Fewer headache attacks; about twice a week, usually in the morning;

Hardly any sudden vertigo attacks; approximately once every two weeks;

Hardly any nausea; approximately once every two weeks;

Pain in eyes/eye sockets completely disappeared.

Over a period of five months on the dosage of six tablets per day (2-2-2 per day), the patient's symptoms reversed and she experienced:

increased frequency of headaches, approximately every two days, several times a day;

increased frequency of vertigo attacks, generally in conjunction with the headache;

symptoms of nausea about once a week;

increased frequency and severity of eye pain, including occasional severity to the point that the patient could not keep her eye open and intense pain when looking up or focusing on an object.

Dosage was increased to 9 tablets per day (3-3-3 per day); a total dosage of 4.5 g per day. Over a subsequent observational period of six months, the patient:

did not have any further attacks of headache;

did not have any attacks of vertigo or dizziness;

had only two short episodes of nausea;

had one episode of pain behind her eyes.

Quality of life was considerably improved such that the subject was able to successfully pass her final examinations at high school. The patient's symptoms improved, particularly in the last few weeks of this treatment period:

Pain in eyes/eye sockets completely disappeared;

Nausea almost completely disappeared.

The patient indicated that her symptoms occur very rarely again and she only experiences occasional attacks of vertigo and headache associated with being tired or stressed or on very hot days, which the patient attributed to her circulation. The patient indicated that drinking water helps alleviate these attacks.

Example 2

Case Study: Administration of Acetyl-Leucine for Vestibular Migraine

Patient Details:
Sex: Female
Age: 18
Treatment:

Six tablets of Tanganil® per day: two in the morning, two at noon and two in the evening. Tanganil® tablets as described in Example 1.

Before treatment with Tanganil® the patient experienced the following symptoms: a total of about 50 attacks of vertigo over a period of four months, each lasting about 20 minutes, 30% of which were accompanied by headache. This resulted in at least three days a week on sick-leave. Three weeks after starting treatment with Tanganil® (2-2-2 per day) the patient had suffered no further attacks. Further follow up revealed no attacks within a period of 14 weeks from the start of treatment.

Example 3

Case Study: Administration of Acetyl-Leucine for Migraine with Aura
  Patient Details:
  Sex: Male
  Age: Adult
  Treatment:
  Ten tablets of Tanganil® per day: four in the morning, three at noon and three in the evening. Tanganil® tablets as described in Example 1.
  Before treatment with Tanganil® the patient experienced the following symptoms for at least one year:
    Left-sided headache attacks lasting many hours, in 20% of which were accompanied by a visual aura, lasting about 5 minutes;
      frequency: about once a week; responding to 600 mg of Ibuprofen which was taken once a week;
    Isolated visual aura in the left hemi field, lasting about 5 minutes;
      frequency about four times a month.
  After beginning treatment with Tanganil®, during a period of two months, the patient only reported one isolated visual aura, one visual aura with migraine headache, and one left-sided migraine headache. Treatment was terminated after two months. Following termination of this two-month treatment period, within a subsequent 4-week period, the patient reported a marked increase in attacks, including six attacks of migraine headache, one with visual aura, and one isolated visual aura. Treatment was subsequently resumed for nearly a year, during which the patient experienced one attack of migraine headache without aura about every two months and one attack of migraine headache with aura about every three months. Treatment was subsequently terminated, and in the six weeks following, the patient experienced five attacks of migraine headache and three attacks with aura.

Example 4

Case Study: Administration of Acetyl-Leucine for Migraine and Vestibular Migraine
  Patient Details:
  Sex: Male
  Age: 54
  Treatment:
  Six tablets of Tanganil® per day: two in the morning, two at noon and two in the evening for one week; thereafter, ten tablets of Tanganil® per day: four in the morning, three at noon and three in the evening. Tanganil® tablets as described in Example 1.
  Before treatment with Tanganil® the patient experienced the following symptoms for at least one year:
    Almost every second day, attacks of migraine headache; no improvement with Ibuprofen or Aspirin; improvement with Novalgin;
    Attacks of vertigo accompanied by headache, frequency about three times a week;
    On extended sick-leave and experienced significant weight loss (12 kg).
  After beginning treatment with Tanganil® (2-2-2, for one week, then 4-3-3 per day), within a period of 4 weeks, the patient reported no attacks of headache any more, and no requirement for pain killers. Headaches recurred when medication was stopped for one day, so treatment was continued.

Example 5

Case Study: Administration of Acetyl-Leucine for Migraines
  Patient Details:
  Sex: Male
  Age: 54
  Treatment:
  Tablets of Tanganil® administered per day as described in Example 4. Tanganil® tablets as described in Example 1.
  Before treatment with Tanganil® the patient experienced the following symptoms for many years:
    Headache attacks lasting three to four hours having a frequency of approximately 20-25 headaches per month;
    Migraine attacks lasting three to four hours having a frequency of approximately three or four per month and migraine attacks with aura once or twice per year.
  During six weeks of treatment with Tanganil®, the patient reported reduced frequency of headache attacks of approximately three per month and reduced frequency of migraine attacks of approximately two per month. The patient experienced an improvement in symptoms within a couple of days of initiating treatment.
  The patient continued taking Tanganil® for six months and then discontinued treatment for three months. In the five weeks following termination of treatment, the patient experienced an increase in frequency of migraine attacks to four per month. The patient resumed treatment with Tanganil® and after three months experienced a reduction in frequency of migraine attacks to two per month.

Example 6

Case Study: Administration of Acetyl-Leucine for Migraines
  Patient Details:
  Age: 38
  Treatment:
  Tablets of Tanganil® administered per day as described in Example 4. Tanganil® tablets as described in Example 1.
  Before treatment with Tanganil® the patient experienced the following symptoms for several years:
    Migraine attacks without aura lasting approximately three days having a frequency of approximately two a month (approximately six migraine-days per month);
    With the migraine attacks, accompanying symptoms included sensitivity to sound and light and sometimes diarrhoea before migraine initiation.
  Before initiation of treatment with Tanganil®, the patient was most recently treated with rizatriptan and naproxen. During nearly eight weeks of treatment with Tanganil®, the patient reported reduced frequency of migraine attacks of approximately four with reduced duration. Two attacks lasted two days and two attacks lasted only one day, compared to three migraine-days experienced per attack before treatment with Tanganil®.
  The patient continued taking Tanganil® and over four months of treatment experienced a reduction of migraine-days from 6 per month to 1.33 per month.

Example 7

Case Study: Administration of Acetyl-Leucine for Vestibular Migraine
  Patient Details:
  Sex: Female
  Age: 70
  Treatment:
  Ten tablets of Tanganil® per day: four in the morning, three at noon and three in the evening. Tanganil® tablets as described in Example 1.

Before treatment with Tanganil® the patient experienced the following symptoms for several years:
  Migraine attacks at a frequency of approximately 3.3 per month;
  Symptoms of vertigo with the attacks.

After beginning treatment with Tanganil®, within a period of eight months, the patient reported a total of ten attacks and a reduction of frequency of attack from approximately 3.3 per month to 1.25 per month. The patient reported that the attacks were shorter and had a lower intensity, including for symptoms of vertigo.

The subject continues taking this dosage. Quality of life is considerably improved.

Example 8

Case Study: Administration of Acetyl-Leucine for Migraines
  Patient Details:
  Sex: Male
  Age: 65
  Treatment:
  Ten tablets of Tanganil® per day: four in the morning, three at noon and three in the evening. Tanganil® tablets as described in Example 1.

Before treatment with Tanganil® the patient experienced the following symptoms for many years:
  Migraine attacks with and without aura, including chronic migraine, at a frequency of approximately 20 per month;
  Daily headaches treated with regular administration of pain killers.

Before initiation of treatment with Tanganil®, the patient was on various medications including nearly daily administration of pain killers, as well as treatment with triptans. After beginning treatment with Tanganil®, within a period of two months, the patient reported weeks without migraine for the first time in many years and without the need for additional medication. The patient reported a reduction of frequency of attack from approximately 20 per month to five per month, with a total of approximately eight headache days per month.

The subject continues taking this dosage. Quality of life is considerably improved.

Example 9

Case Study: Administration of Acetyl-Leucine for Migraines
  Patient Details:
  Sex: Female
  Age: 27
  Treatment:
  Ten tablets of Tanganil® per day: four in the morning, three at noon and three in the evening. Tanganil® tablets as described in Example 1.

Before treatment with Tanganil® the patient experienced the following symptoms for many years:
  Migraine attacks without aura at a frequency of approximately 12 per month;
  Almost daily headaches.

After beginning treatment with Tanganil®, the patient reported a reduction of frequency of migraine attack from approximately 12 per month to four per month and a reduction of headache-days per month to four.

The subject continues taking this dosage. Quality of life is considerably improved.

Example 10

NPC Chinese Hamster Ovary (CHO) cells were treated in vitro for 72 hours with 1 mM of acetyl-DL-leucine, acetyl-L-leucine, acetyl-D-leucine, DL-leucine, L-leucine, and D-leucine, respectively. Relative lysosomal volume was quantified via LysoTracker.

The NPC CHO cells were observed to have elevated LysoTracker fluorescence levels relative to wild-type controls, which is indicative of increased lysosomal volume of the diseased phenotype.

Figure 1:
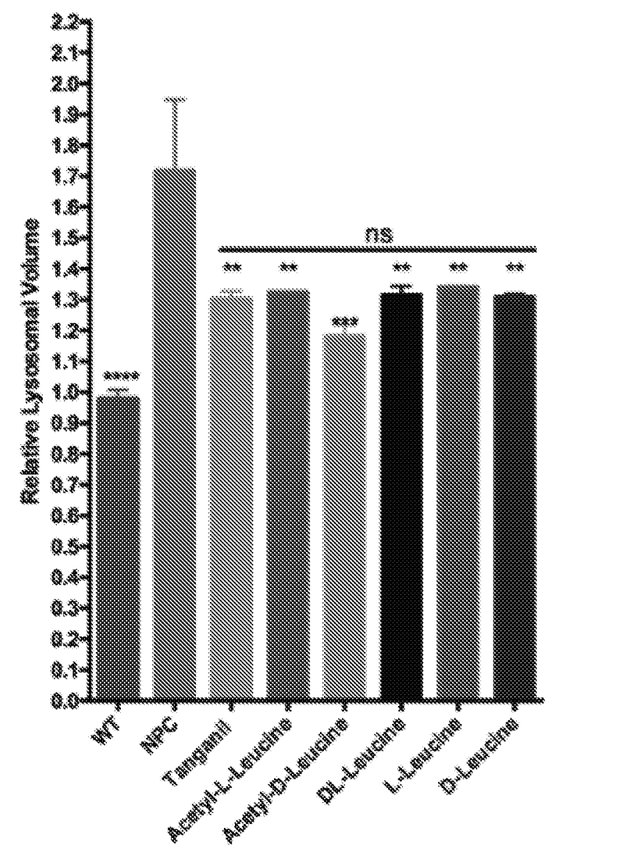
FIG. 1 demonstrates leucine's and acetyl-leucine's similar activity when exposed to Niemann-Pick type C (NPC)-diseased Chinese Hamster Ovary (CHO) cells in vitro.

Treatment of the NPC CHO cells with each of acetyl-DL-leucine, acetyl-L-leucine, acetyl-D-leucine, DL-leucine, L-leucine, and D-leucine significantly reduced lysosomal volume in the cells. Data presented in FIG. 1 show the results for each treatment, with lysosomal volume expressed as fold change relative to untreated wild-type fibroblasts. The asterisks (**) indicate a p-values of <0.01 versus untreated NPC1-null.

The data shows that leucine and acetyl-leucine demonstrated similar activity in vitro and were both associated with the rectification of disturbed lysosomal storage by reducing lysosomal volume.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The entire disclosure of each of the patent documents and scientific articles referred to herein is incorporated by reference for all purposes.

REFERENCES

Aminoff, Roger P. Simon, David A. Greenberg, Michael J. (2009). Clinical neurology (7 ed.). New York, N.Y.: Lange Medical Books/McGraw-Hill. pp. 85-88;
Armstrong, C.; American Academy of Neurology, American Headache Society (15 Apr. 2013); "*AAN/AHS update recommendations for migraine prevention in adults*"; American family physician 87 (8): 584-5;
Bartleson J. D., Cutrer F. M. (May 2010); "*Migraine update; Diagnosis and treatment*"; Minn Med. 93 (5): 36-41;
Becker-Bense et al (2015) Abstract EAN;
Bose P. I., Goadsby P. J.; 2016; "*The migraine postdrome*"; Curr Opin Neurol, June; 29(3):299-301;
Bremova et al. (2015) Neurology; 85(16): 1368-75;
Buzzi, M. G.; Cologno, D.; Formisano, R.; Rossi, P. (October-December 2005); "*Prodromes and the early phase of the migraine attack: therapeutic relevance*"; Functional Neurology, 20 (4): 179-83;
Cheng et al., "Highly Stabilized Curcumin Nanoparticles Tested in an In Vitro Blood-Brain Barrier Model and in Alzheimer's Disease Tg2576 Mice," The AAPS Journal, vol. 15, no. 2, pp. 324-336 (2013);
Colman I., Friedman B. W., Brown M. D., et al. (June 2008); "*Parenteral dexamethasone for acute severe migraine headache: meta-analysis of randomised controlled trials for preventing recurrence*"; BMJ. 336 (7657): 1359-61;
Derry, S.; Rabbie, R.; Moore, R. A. (2013 Apr. 30); "*Diclofenac with or without an antiemetic for acute migraine headaches in adults*"; The Cochrane Database of Systematic Reviews (4): CD008783;
Ferber-Viart et al. (2009) Audiol Neurootol; 14(1): 17-25;

Gilmore, B.; Michael, M. (2011 Feb. 1); "*Treatment of acute migraine headache*"; American family physician; 83 (3): 271-80;

Gunther et al. (2015) PLoS One; 10(3): e0120891;

Hanson et al., "Intranasal delivery bypasses the blood-brain barrier to target therapeutic agents to the central nervous system and treat neurodegenerative disease," BMC Neurosci. 9(Suppl 3):S5 (2008);

Headache Classification Subcommittee of the International Headache Society (2004); "*The International Classification of Headache Disorders: 2nd edition*", Cephalalgia. 24 (Suppl 1): 9-160;

Kabanov et al., "New Technologies for Drug Delivery across the Blood Brain Barrier," Curr Pharm Des., 10(12):1355-1363 (2004);

Kelman L. (February 2006); "*The postdrome of the acute migraine attack*"; Cephalalgia. 26 (2): 214-20;

Kirthi, V.; Derry, S.; Moore, R. A. (2013 Apr. 30); "*Aspirin with or without an antiemetic for acute migraine headaches in adults*"; The Cochrane Database of Systematic Reviews (4): CD008041;

Lände et al. "Production of L-Leucine Nanoparticles under Various Conditions Using an Aerosol Flow Reactor Method," Journal of Nanomaterials, vol. 2008, article ID 680897 (2008);

Lempert, T, et al; (2012) Journal of Vestibular Research 22; 167-172;

Oleson (Editor); "*The Headaches*"; 3$^{rd}$ Edition; 2006;

Ory et al., "Intrathecal 2-hydroxypropyl-β-cyclodextrin decreases neurological disease progression in Niemann-Pick disease, type C1: a non-randomised, open-label, phase 1-2 trial," Vol. 390, Issue 10104, pp. 1758-1768 (2017);

Pelz et al. (2015) J Neurol; 262(5): 1373-5;

Patel et al., "Crossing the Blood-Brain Barrier: Recent Advances in Drug Delivery to the Brain," CNS Drugs 31:109-133 (2017);

Rabbie, R.; Derry, S.; Moore, R. A. (30 Apr. 2013); "*Ibuprofen with or without an antiemetic for acute migraine headaches in adults*"; The Cochrane Library, Wiley (4): CD008039;

Rae-Grant, [edited by] D. Joanne Lynn, Herbert B. Newton, Alexander D. (2004); The 5-minute neurology consult. Philadelphia: Lippincott Williams & Wilkins; p. 26; CS1 maint: Extra text: authors list (link)

Rossi, P; Ambrosini, A; Buzzi, M G (October-December 2005); "*Prodromes and predictors of migraine attack*"; Functional neurology. 20 (4): 185-91; PMID 16483459;

Samuels, A. H. Ropper, M. A. (2009); Adams and Victor's principles of neurology (9 Ed.). New York: McGraw-Hill Medical; pp. Chapter 10;

Schniepp et al (2015) Cerebellum; 3:8;

Slap, G. B. (2008); Adolescent medicine; Philadelphia, Pa.: Mosby/Elsevier, p. 105;

Strupp et al (2013) J Neurol; 260(10): 2556-61;

Tepper S. J, Deborah E. (April 2010); "*Breaking the cycle of medication overuse headache*"; Cleveland Clinic Journal of Medicine; 77 (4): 236-42;

Tintinalli, J. E. (2010); Emergency Medicine: A Comprehensive Study Guide (Emergency Medicine (Tintinalli)); New York: McGraw-Hill Companies; pp. 1116-1117;

Vibert et al (2001), Eur J Neurosci; 13(4): 735-48;

Zwergal et al (2016) Brain Struct Funct; 221(1): 159-70.

The invention claimed is:

1. A method of treating or preventing a migraine, or one or more symptoms associated therewith, in a subject, said method consisting of administering to the subject a therapeutically or prophylactically effective amount of acetyl-leucine, or a pharmaceutically acceptable salt thereof, wherein the migraine is not associated with vertigo or symptoms of vertigo.

2. The method according to claim 1, wherein the subject is a human.

3. The method of claim 1, comprising administering to the subject a therapeutically effective amount of acetyl-leucine, or a pharmaceutically acceptable salt thereof.

4. The method according to claim 1, wherein the acetyl-leucine, or pharmaceutically acceptable salt thereof, reduces the frequency of, alleviates, or eliminates one or more symptoms associated with a migraine comprising headache, tiredness, aura, nausea, vomiting, sensitivity to light, sensitivity to sound, sensitivity to smell, sweating, poor concentration, feeling hot, feeling cold, abdominal pain, or diarrhoea.

5. The method according to claim 4, wherein the acetyl-leucine, or pharmaceutically acceptable salt thereof, reduces the frequency of, alleviates, or eliminates a headache.

6. The method according to claim 4, wherein the acetyl-leucine, or pharmaceutically acceptable salt thereof, reduces the frequency of, alleviates or eliminates an aura.

7. The method according to claim 6, wherein the aura occurs with a headache.

8. The method according to claim 6, wherein the aura occurs without a headache.

9. The method of claim 6, wherein the acetyl-leucine, or pharmaceutically acceptable salt thereof, reduces the frequency of, alleviates or eliminates one or more symptoms of the aura comprising visual problems or disturbances, numbness or tingling, motor problems, speech difficulties, or loss of consciousness.

10. The method of claim 6, wherein the acetyl-leucine, or pharmaceutically acceptable salt thereof, treats or prevents pain associated with a migraine.

11. The method of claim 1, wherein the migraine is a hemiplegic migraine.

12. The method of claim 1, wherein the migraine is a sporadic hemiplegic migraine.

13. The method of claim 1, wherein the migraine is a vestibular migraine.

14. The method of claim 1, wherein the migraine is a basilar-type migraine.

15. The method of claim 1, wherein the migraine is a retinal migraine.

16. The method of claim 1, wherein the migraine is chronic migraine.

17. The method of claim 1, wherein the migraine is episodic migraine.

18. The method of claim 3, wherein the acetyl-leucine is in racemic form.

19. The method of claim 3, wherein the acetyl-leucine is in an enantiomeric excess of the L-enantiomer.

20. The method of claim 3, wherein the acetyl-leucine is administered in a dose of from about 500 mg to about 15 g per day.

* * * * *